United States Patent
Cole et al.

(10) Patent No.: US 8,562,674 B2
(45) Date of Patent: *Oct. 22, 2013

(54) FRONT LOADING IOL INSERTION APPARATUS AND METHOD OF USING

(75) Inventors: Mark S. Cole, Trabuco Canyon, CA (US); Rod T. Peterson, Santa Ana, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1636 days.

This patent is subject to a terminal disclaimer.

(21) Appl. No.: 11/056,501

(22) Filed: Feb. 11, 2005

(65) Prior Publication Data

US 2006/0184181 A1    Aug. 17, 2006

(51) Int. Cl.
*A61F 2/16* (2006.01)

(52) U.S. Cl.
USPC .......................................... 623/6.12; 607/107

(58) Field of Classification Search
USPC ................... 623/6.12; 606/107, 17
See application file for complete search history.

(56) References Cited

U.S. PATENT DOCUMENTS

| | | | |
|---|---|---|---|
| 4,205,747 A * | 6/1980 | Gilliam et al. ................ | 206/5.1 |
| 4,862,885 A | 9/1989 | Cumming | |
| 5,275,604 A | 1/1994 | Rheinish et al. | |
| 5,281,227 A | 1/1994 | Sussman | |
| 5,304,182 A | 4/1994 | Rheinish et al. | |
| 5,425,734 A | 6/1995 | Blake | |
| 5,468,246 A | 11/1995 | Blake | |
| 5,616,148 A | 4/1997 | Eagles et al. | |
| 5,620,450 A | 4/1997 | Eagles et al. | |
| 5,728,102 A | 3/1998 | Feingold et al. | |
| 5,772,666 A | 6/1998 | Feingold et al. | |
| 5,807,400 A | 9/1998 | Chambers et al. | |
| 5,860,984 A | 1/1999 | Chambers et al. | |
| 5,902,307 A | 5/1999 | Feingold et al. | |
| 6,010,510 A | 1/2000 | Brown et al. | |
| 6,048,347 A | 4/2000 | Erdman | |
| 6,056,757 A | 5/2000 | Feingold et al. | |
| 6,143,000 A | 11/2000 | Feingold | |
| 6,162,229 A | 12/2000 | Feingold et al. | |
| 6,174,315 B1 | 1/2001 | Chambers et al. | |
| 6,203,549 B1 | 3/2001 | Waldock | |

(Continued)

FOREIGN PATENT DOCUMENTS

| BE | 1016692 A3 | 4/2007 |
|---|---|---|
| EP | 270257 | 8/1988 |

(Continued)

*Primary Examiner* — Ryan Severson
*Assistant Examiner* — Rachel S Papeika
(74) *Attorney, Agent, or Firm* — Abbott Medical Optics Inc.

(57) ABSTRACT

An insertion system is provided for delivering an intraocular lens into an eye. The insertion system has an inserter for delivering the lens and a lens case for holding the lens prior to delivery. The inserter has a handpiece having a longitudinal axis, a proximal end, and a distal end. The inserter also has a nosepiece disposed at the distal end of the inserter, the nosepiece having a rotational axis that is substantially perpendicular to the longitudinal axis and a load chamber with a transfer interface for receiving the lens. The case has a transfer port for transferring the lens from the case into the load chamber. Once the lens is transferred into the load chamber, the nosepiece is adapted to rotate approximately 180 degrees about the rotational axis between a first position for loading the lens and a second position for delivering the lens into the eye.

26 Claims, 7 Drawing Sheets

(56) References Cited

U.S. PATENT DOCUMENTS

| | | |
|---|---|---|
| 6,214,015 B1 | 4/2001 | Reich et al. |
| 6,228,094 B1 | 5/2001 | Erdman |
| 6,241,737 B1 | 6/2001 | Feingold |
| 6,248,170 B1 | 6/2001 | Sirejacob |
| 6,336,932 B1 | 1/2002 | Figueroa et al. |
| 6,371,960 B2 | 4/2002 | Heyman et al. |
| 6,386,357 B1 | 5/2002 | Egawa |
| 6,387,101 B1 | 5/2002 | Butts et al. |
| 6,406,481 B2 | 6/2002 | Feingold et al. |
| 6,468,282 B2 | 10/2002 | Kikuchi et al. |
| 6,471,708 B2 | 10/2002 | Green |
| 6,491,697 B1 | 12/2002 | Clark et al. |
| 6,506,195 B2 | 1/2003 | Chambers et al. |
| 6,537,283 B2 | 3/2003 | Van Noy |
| 6,558,395 B2 | 5/2003 | Hjertman et al. |
| 6,685,740 B2 | 2/2004 | Figueroa et al. |
| 6,712,848 B1 | 3/2004 | Wolf et al. |
| 7,156,854 B2 | 1/2007 | Brown et al. |
| 7,476,230 B2 * | 1/2009 | Ohno et al. .................. 606/107 |
| 7,754,953 B2 | 7/2010 | Takegawa |
| 2001/0001822 A1 | 5/2001 | Chambers et al. |
| 2001/0015593 A1 | 8/2001 | Polla et al. |
| 2001/0041897 A1 | 11/2001 | Feingold et al. |
| 2002/0022881 A1 | 2/2002 | Figueroa et al. |
| 2002/0077633 A1 | 6/2002 | Kikuchi et al. |
| 2002/0082609 A1 | 6/2002 | Green |
| 2002/0151904 A1 | 10/2002 | Feingold et al. |
| 2002/0193805 A1 | 12/2002 | Ott et al. |
| 2003/0036765 A1 | 2/2003 | Van Noy |
| 2003/0045930 A1 | 3/2003 | Nguyen |
| 2003/0050646 A1 | 3/2003 | Kikuchi et al. |
| 2003/0212406 A1 | 11/2003 | Kobayashi et al. |
| 2003/0212409 A1 | 11/2003 | Kobayashi et al. |
| 2004/0127911 A1 | 7/2004 | Figueroa et al. |
| 2004/0193121 A1 | 9/2004 | Kadziauskas |
| 2004/0243141 A1 * | 12/2004 | Brown et al. .................. 606/107 |
| 2004/0267359 A1 | 12/2004 | Makker et al. |
| 2005/0125000 A1 | 6/2005 | Tourrette et al. |
| 2006/0085013 A1 * | 4/2006 | Dusek et al. .................. 606/107 |
| 2006/0149315 A1 | 7/2006 | Kebel et al. |
| 2007/0060925 A1 | 3/2007 | Pynson |
| 2008/0058830 A1 | 3/2008 | Cole et al. |
| 2008/0097459 A1 | 4/2008 | Kammerlander et al. |
| 2008/0114313 A1 | 5/2008 | Gomez et al. |
| 2009/0125034 A1 * | 5/2009 | Pynson .................. 606/107 |
| 2010/0217273 A1 | 8/2010 | Someya et al. |
| 2010/0228260 A1 | 9/2010 | Callahan et al. |
| 2010/0278261 A1 | 11/2010 | Chujoh et al. |
| 2012/0022549 A1 | 1/2012 | Someya et al. |
| 2012/0071887 A1 | 3/2012 | Ichinohe et al. |

FOREIGN PATENT DOCUMENTS

| | | |
|---|---|---|
| EP | 0 402 138 | 12/1990 |
| EP | 0 467 814 | 1/1992 |
| EP | 1338254 | 8/2003 |
| EP | 1 481 652 A1 | 1/2004 |
| EP | 1 421 917 A2 | 5/2004 |
| EP | 1360944 B1 | 9/2007 |
| EP | 2161005 A1 | 3/2010 |
| EP | 1737393 B1 | 6/2010 |
| EP | 2123239 B1 | 3/2012 |
| FR | 2 875 126 | 3/2006 |
| JP | 4707016 B2 | 6/2011 |
| WO | 94/22402 | 10/1994 |
| WO | WO96/28121 | 9/1996 |
| WO | WO97/15253 | 1/1997 |
| WO | WO99/33411 | 8/1999 |
| WO | WO99/58086 | 11/1999 |
| WO | 01/74427 | 10/2001 |
| WO | WO 01/87186 A1 | 11/2001 |
| WO | WO0187187 A1 | 11/2001 |
| WO | WO03024356 A2 | 3/2003 |
| WO | WO2004/045467 | 3/2004 |
| WO | WO2004/010903 | 5/2004 |
| WO | WO2005020853 A2 | 3/2005 |
| WO | WO 2005/030097 A1 | 4/2005 |
| WO | WO2005070341 A1 | 8/2005 |
| WO | WO 2006070219 | 7/2006 |
| WO | WO2006086495 A1 | 8/2006 |
| WO | WO2007028368 A1 | 3/2007 |
| WO | WO2007087641 A2 | 8/2007 |
| WO | WO2008014260 A1 | 1/2008 |
| WO | WO2008060869 A2 | 5/2008 |

* cited by examiner

FRONT LOADING IOL INSERTION APPARATUS AND METHOD OF USING

BACKGROUND OF THE INVENTION

1. Field of the Invention

The present invention relates to devices, systems, and methods for delivering an intraocular lens into an eye. More particularly, the invention relates to devices, systems, and methods in which the intraocular lens is loaded from the front end of the device.

2. Description of the Related Art

Intraocular lenses (IOLs) may be implanted in the eye of a subject to replace the natural crystalline lens or to otherwise modify the vision of an eye containing either the natural lens or another IOL. IOLs often include an optic and one or more flexible fixation members or haptics extending from the optic to secure and center the optic within the eye. When the IOL replaces the natural lens, the natural lens must first be removed, for instance, using a phacoemulsification system. The IOL is then generally implanted using an insertion apparatus or device that rolls, folds, or otherwise configures the lens for delivery through a small incision in the eye in a way that reduces trauma and expedites post-surgery healing.

Inserters for delivering IOLs into the eye generally employ a cartridge having a hollow insertion tube or cannula through which the folded IOL is passed using a pushrod. The inserter may be designed for reuse, in which case the inserter components are usually made of some type of metal alloy. Alternatively, disposable inserters may be used that are made of less expensive materials, such as plastics, and that remain in a sterile package until ready for use. The pushrod and insertion tube may be designed to advantageously provide the surgeon precise control of the IOL as it is place inside the eye, for example as disclosed in U.S. Pat. No. 6,093,193, herein incorporated by reference.

One problem encountered with existing inserters is difficulty in loading the IOL into the inserter. The IOL is typically about 10 to 15 mm in diameter, about a millimeter thick, and is manually delivered from a sterile container to a cartridge or inserter using forceps or tweezers. Manual transfer of the IOL presents difficulties in maintaining both sterility of the IOL and the correct orientation of the IOL within the cartridge or inserter. Improper orientation of the IOL can cause damage to the IOL or inadequate surgeon control during delivery into the eye.

These problems may be mitigated by preloading the IOL at the manufacturer into a cartridge or container that is designed to be directly attached to the inserter. The cartridge or container may be attached to the inserter either at the manufacturer or by the user prior to surgery. In either case, the IOL is generally not stored directly in the inserter, since it is desirable that the IOL be maintained during storage in an unstressed state in order to prevent undesirable, permanent deformation of the optic element. Thus, some type of loading process is still generally necessary to transfer the IOL into the inserter.

Various means and mechanisms are disclosed in the art for manipulating the IOL from a state suitable for storage of the IOL to a state suitable for delivery of the IOL into the eye of a patient. Prior to transferring the IOL into the inserter, the IOL is maintained in an unstressed state inside some type of holding chamber that is attached above or to the side of a chamber that is directly in line with the pushrod. In transferring the IOL from the holding chamber and into the pushrod path, the IOL is move along an axis that is normal to the longitudinal axis of travel of the pushrod. Such designs require relatively complex mechanisms to move IOL along two substantially orthogonal axes (i.e., the transfer axis of travel and the pushrod longitudinal axis of travel). Another potential problem with such loading configurations is that the mechanisms for transferring the IOL may fail to provide adequate visibility of the IOL within the inserter. Inadequate visibility of the IOL makes it more difficult to ensure proper orientation and lubrication of the IOL prior to delivery through the insertion tube.

It would be advantageous to provide IOL insertion apparatus and methods that facilitate the transfer and/or placement of an IOL within the inserter in preparation for delivery into the eye of a subject during an ocular surgery, such as a cataract surgery.

SUMMARY OF THE INVENTION

The present invention, which relates to devices, systems, and methods for delivering an intraocular lens into an eye, addresses the above problems by maintaining an intraocular lens inside a lens case prior to use. The intraocular lens is then transferred from the lens case and into the nosepiece of an inserter in preparation for insertion into the eye of a subject eye.

One aspect of the present invention involves an insertion system for delivering an intraocular lens into the eye of a subject. The insertion system comprises an inserter for delivering an intraocular lens into an eye having a handpiece, a nosepiece, and a lens case for holding the intraocular lens. The handpiece has a longitudinal axis, a proximal end, and a distal end. The nosepiece is disposed at the distal end and has a rotational axis substantially perpendicular to the longitudinal axis and a load chamber with a transfer interface for receiving the intraocular lens. The nosepiece is adapted to rotate approximately 180 degrees about the rotational axis between a first position for loading the intraocular lens and a second position for delivering the intraocular lens into the eye of a subject. The lens case has a transfer port for transferring the intraocular lens from the lens case into the load chamber. The inserter may further comprise a pushrod for moving the intraocular lens through the load chamber.

The nosepiece may further comprise a delivery channel for delivering the intraocular lens into the eye, the delivery channel preferably having a delivery port with a cross-sectional area that is less than the cross-sectional area of the load chamber. The delivery channel may comprise a smoothly tapered portion extending from the load chamber and is preferably substantially disposed along the longitudinal axis when the nosepiece is disposed in the first position and when the nosepiece is disposed in the second position. The transfer interface of the load chamber preferably comprises an aperture that is substantially center along the longitudinal axis and distally located relative to the delivery channel when the nosepiece is in the first position.

In one embodiment, the pushrod is adapted to manipulate a haptic of the intraocular lens. In other embodiments, the nosepiece moves or is rotated from the first position to the second position in an automated fashion. In yet other embodiments, the insertion system comprises a container for enclosing at least one inserter and/or lens case. The container may be stored and/or shipped.

In another aspect of the invention, an inserter for delivering an intraocular lens into an eye comprises a handpiece and a nosepiece. The handpiece has a longitudinal axis substantially centered within the handpiece, a proximal end, and a distal end. The nosepiece is disposed at the distal end and has a longitudinal axis. The nosepiece also has a load chamber with a transfer interface for receiving an intraocular lens and is movable between a first position for loading the intraocular lens and a second position for delivering the intraocular lens into the eye of a subject. The longitudinal axis of the handpiece and the longitudinal axis of the nosepiece are substantially coaxial when the nosepiece is in either the first position or the second position.

In certain embodiments, the inserter includes an offset angle between the longitudinal axis of the handpiece and the longitudinal axis of the nosepiece when the nosepiece is in at least one of the first position and the second position. The offset angle is preferably less than at least about 10 degrees and more preferably less than about 1 degree.

In yet another aspect of the invention, an inserter for delivering an intraocular lens into an eye comprises a handpiece and a nosepiece. The handpiece has a longitudinal axis substantially centered within the handpiece, a proximal end, and a distal end. The nosepiece is disposed at the distal end and has a rotational axis substantially perpendicular to the longitudinal axis. The nosepiece also has a load chamber with a transfer interface for receiving an intraocular lens, the rotational axis substantially intersecting the longitudinal axis. The nosepiece is adapted to rotate about the rotational axis between a first position for loading the intraocular lens and a second position for delivering the intraocular lens into the eye of a subject.

In still another aspect of the present invention, a surgical system for performing an ocular surgery comprises a phacoemulsification system having a first handpiece for removing the natural lens of an eye and an electronic controller for controlling at least one of the fluidics of the first handpiece and power into the first handpiece. The surgical system further comprises at least one inserter for delivering an intraocular lens into the eye and at least one lens case for holding the intraocular lens. The at least one inserter has a second handpiece and a nosepiece. The second handpiece has a longitudinal axis, a proximal end, and a distal end. The nosepiece is disposed at the distal end and has a rotational axis substantially perpendicular to the longitudinal axis and a load chamber with a transfer interface for receiving the intraocular lens. The nosepiece is adapted to rotate approximately 180 degrees about the rotational axis between a first position for loading the intraocular lens and a second position for delivering the intraocular lens into the eye of a subject. The at least one lens case has a transfer port for transferring the intraocular lens from the lens case into the load chamber. The surgical system may comprise more than one inserter and lens case.

In yet another aspect of the present invention, a method of packaging an insertion system for delivery of an intraocular lens into the eye of a subject comprises providing an inserter for delivering an intraocular lens into an eye. The method further comprises providing a lens case for holding the intraocular lens and having a transfer port for transferring the intraocular lens from the lens case into a load chamber of the inserter. The method additionally comprises enclosing the inserter and lens case within a container. The method may further comprise enclosing an intraocular lens inside the lens case and storing the container and/or shipping the container.

In yet another aspect of the present invention, a method of delivering an intraocular lens into the eye of a subject comprises providing an insertion system having a handpiece with a longitudinal axis, a nosepiece with a rotational axis, and a lens case. The method also comprises disposing the nosepiece in a first position in which a delivery channel of the nosepiece is disposed along the longitudinal axis and operably connecting a transfer port of the lens case with a transfer interface of the load chamber. The method further comprises transferring the intraocular lens from the lens case into the load chamber and then disengaging the lens case from the nosepiece. The method additionally comprises rotating the nosepiece about the rotational axis to a second position suitable for delivering the intraocular lens into an eye of a subject.

In certain embodiments, the method further comprises providing a phacoemulsification system and removing a natural lens from the eye of a subject. In such embodiments, the method may further comprise delivering the intraocular lens into the eye of a subject. In other embodiments, rotating the nosepiece to a second position transversely displaces at least a portion of a haptic of the lens from a pushrod. In yet other embodiments, the handpiece further comprises a pushrod and rotating is performed in an automated fashion as a tip of the pushrod traverses the longitudinal axis.

BRIEF DESCRIPTION OF THE DRAWINGS

Embodiments of the present invention will be better understood from the following detailed description when read in conjunction with the accompanying drawings. Such embodiments, which are for illustrative purposes only, depict the novel and non-obvious aspects of the invention. The drawings include the following 12 figures, with like numerals indicating like parts.

DETAILED DESCRIPTION OF THE DRAWINGS

Figure 1:
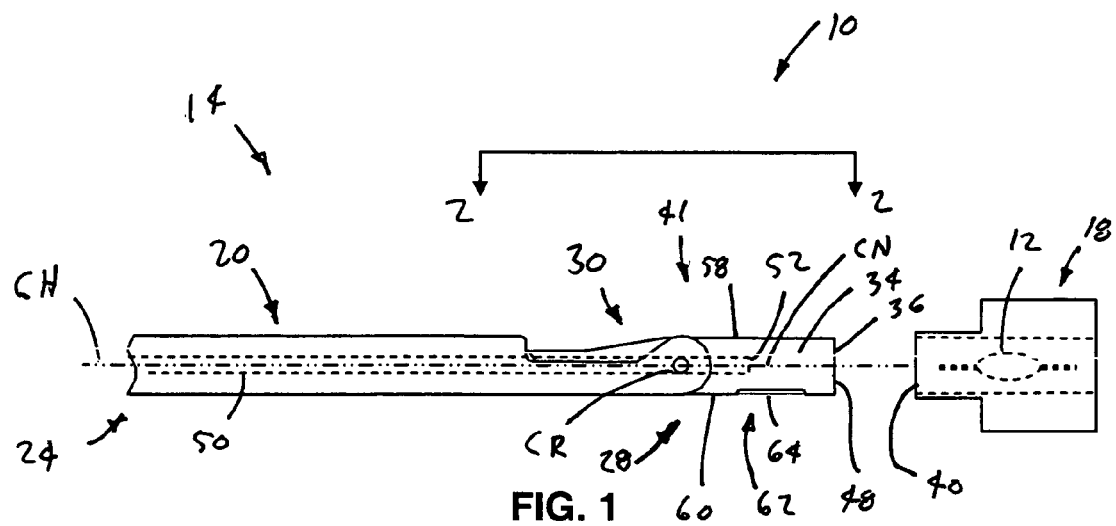
FIG. 1 is a side view of an insertion system according to an embodiment of the invention showing a nosepiece disposed in a first position.

Referring to FIGS. 1-6, in certain embodiments, an insertion system 10 for delivering an intraocular lens 12 into the eye of a subject comprises an inserter 14 for delivering the intraocular lens 12 and a lens case 18 for holding the intraocular lens 12 prior to delivery into the eye. The inserter 14 comprises handpiece 20 having a longitudinal axis CH, a proximal end 24, and a distal end 28. The inserter 14 further comprises a nosepiece 30 disposed at the distal end 28 of the inserter 14. The nosepiece 30 has a rotational axis CR that is substantially perpendicular to the longitudinal axis CH and a load chamber 34 with a transfer interface 36 for receiving the intraocular lens 12. The lens case 18 has a transfer port 40 for transferring the intraocular lens 12 from the lens case 18 and into the load chamber 34.

Figure 4:
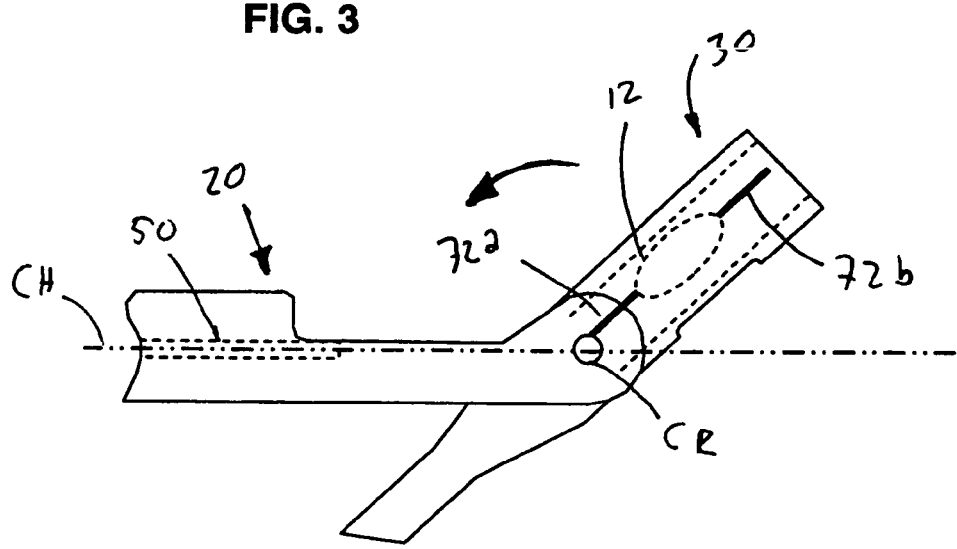
FIG. 4 is a magnified view of the insertion system illustrated in FIG. 1 showing the nosepiece disposed in an intermediate position.
Figure 5:
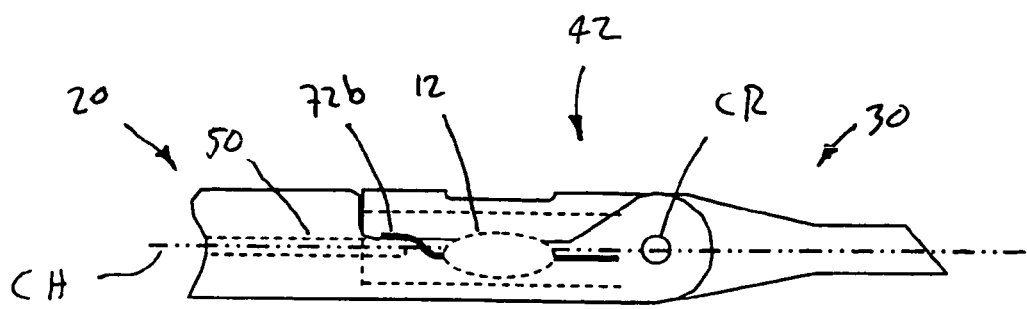
FIG. 5 is a magnified view of the insertion system illustrated in FIG. 1 showing the nosepiece disposed in a second position.
Figure 6:
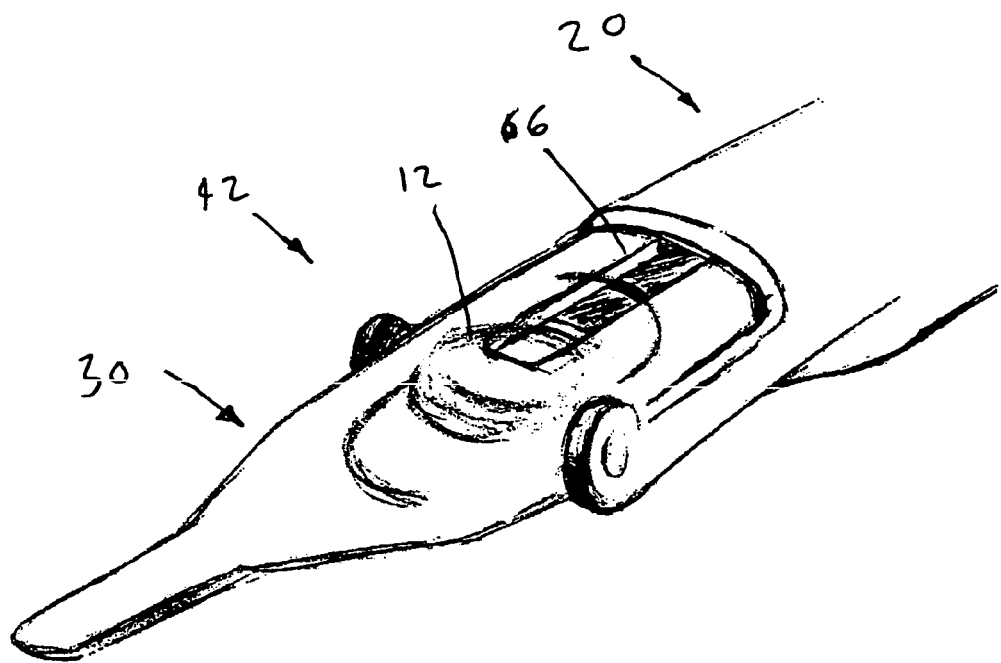
FIG. 6 is a perspective view of an insertion system according to an embodiment of the invention showing an intraocular lens disposed for insertion into the eye of a subject.

The nosepiece 30 is adapted to move or rotate between a first position 41 suitable for loading the intraocular lens 12 (illustrated in FIG. 1) and a second position 42 suitable for delivering the intraocular lens 12 into the eye (illustrated in FIG. 5). For example, the nosepiece 30 may be adapted to rotate approximately 180 degrees about the rotational axis CR between the first position 41 and the second position 42 (compare FIGS. 1, 4, and 5). In certain embodiments, the nosepiece 30 may be adapted for placement in intermediate positions between the first and second positions 41, 42 and/or beyond the first position 41 or the second position 42. For example, an intermediate position between the first and second positions 41, 42 might be utilized for insertion of a viscoelastic or other substance either before and/or after loading of the intraocular lens 12 into the nosepiece 30.

Prior to use by a practitioner, the intraocular lens 12 is preferably disposed inside the lens case 18. The lens case 18 may be used to secure and protect the intraocular lens 12 during shipment from the manufacturer and for storage of the intraocular lens 12 over an extended period of time, preferably over a period of at least about six months, more preferably over a period of at least one year, even more preferably over a period of at least 2 years to at least 4 years. The lens case 18 preferably maintains the intraocular lens 12 in a non-stress or low-stress condition in order to prevent permanent deformation of the intraocular lens 12 that could result in undesirable optical effects or aberrations after placement inside an eye. The interior of the lens case 18 may be filled with a substances such as a liquid or gel; for example, a viscoelastic material. Such substances may be supplied prior to shipment by the manufacturer or by a practitioner prior to transfer into the inserter 14 and may be used, for example, to protect or preserve the intraocular lens 12 or to maintain the intraocular lens 12 in non-stress or low stress condition.

The lens case 18 is preferably made of plastic material suited for storage and protection of the intraocular lens 12 that may be disposed of after use (e.g., after transfer of the intraocular lens 12 into the load chamber 34). Alternatively, portions of the lens case 18 or the entire lens case 18 may be made of a metal material or some other material that may be used to increase the strength, durability, or function of the lens case 18 or of one or more of its components. In such embodiments, the lens case may subsequently be loaded with another intraocular lens.

The inserter 14 may be constructed for delivery of any of the various types of intraocular lenses known in the art. For example, the intraocular lens 12 may be a foldable lens made of at least one of the materials commonly used for resiliently deformable or foldable optics, such as silicone polymeric materials, acrylic polymeric materials, hydrogel-forting polymeric materials, such as polyhydroxyethylmethacrylate, polyphosphazenes, polyurethanes, and mixtures thereof and the like. In one embodiment, the inserter 14 is used with an intraocular lens 12 having an optical zone that is made of SENSAR® brand of acrylic. Other advanced formulations of silicone, acrylic, or mixtures thereof are also anticipated. Selection parameters for suitable lens materials are well known to those of skill in the art. See, for example, David J. Apple, et al., Intraocular Lenses: Evolution, Design, Complications, and Pathology, (1989) William & Wilkins. The lens material preferably has a refractive index allowing a relatively thin, and preferably flexible optic section, for example, having a center thickness in the range of about 150 microns to about 1000 microns, depending on the material and the optical power of the intraocular lens 12. At least portions of the intraocular lens 12, for example one or more haptics or fixation members, may be constructed of a more rigid material including such polymeric materials as polypropylene, polymethylmethacrylate PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitinol, and the like.

The inserter 14 may be configured to deliver any of the various types of intraocular lenses used in the art. For example, the inserter 14 may be used to deliver intraocular lenses having either a single focus or producing two or more foci using refraction, diffraction, or some combination thereof. The inserter 14 may also be used to deliver an accommodating intraocular lens or system of lenses, either together or separately. The inserter 14 may be configured to deliver the intraocular lens 12 into the capsular bag of the eye or into some other portion of the eye, such as the anterior chamber of the eye. The inserter 14 may be used to deliver the intraocular lens 12 into either a phakic or aphakic eye. Additionally, the inserter 14 may be used to deliver the intraocular lens 12 into the eye of a subject already having an intraocular lens located either in the capsular bag or otherwise located within or on the eye.

The transfer port 40 of lens case 18 may be used during transfer of the intraocular lens 12 and is configured to couple the transfer interface 36 of load chamber 34. The transfer port 40 may further comprise a cover (not visible) for sealing the interior of the lens case 18. The cover may be manually removed just prior to transfer of the intraocular lens 12 into the load chamber 34. Alternatively, the cover may be constructed to automatically move out of the way to allow transfer of the intraocular lens 12 when the lens case 18 engages the nosepiece 30.

Figure 2:
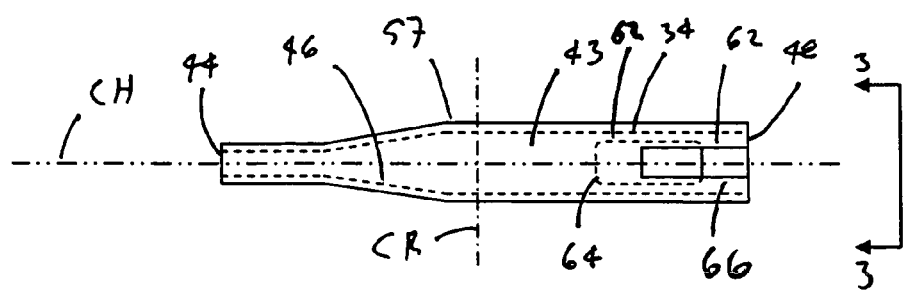
FIG. 2 is a top view of a nosepiece of the insertion system illustrated in FIG. 1.

As illustrated in FIG. 2, the nosepiece 30 further comprises a delivery channel 43 for delivering the intraocular lens 12 into the eye, the delivery channel 43 having a delivery port 44 with a cross-sectional area that is preferably less than a cross-sectional area of the load chamber 34. Unless otherwise indicated, the term "cross-sectional area," as used herein, means the area of a referenced element in a plane that is perpendicular to the longitudinal axis CH of the handpiece 20. The delivery channel 43 preferably comprises a smoothly tapered portion 46 extending from the load chamber 34 and is substantially disposed along the longitudinal axis CH when the nosepiece 30 is disposed in the first position 41 and when the nosepiece 30 is disposed in the second position 42. The smoothly tapered portion 46 may be used to compress and form the intraocular lens 12 into an elongated configuration suitable for delivery into the eye through the delivery port 44.

Figure 3:
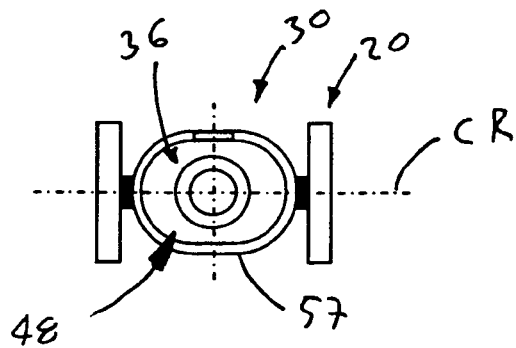
FIG. 3 is an end view of the insertion system illustrated in FIG. 1.

Referring to FIG. 3, the interface 36 of the nosepiece 30 may comprise an aperture 48 that is preferably substantially centered about the longitudinal axis CH and distally located relative to the delivery channel 43 when the nosepiece 30 is in the first position 41. The interface 36 may alternatively or additionally comprise other elements or means, such as a cover, for providing protection of the intraocular lens 12 and/or for providing transfer of the intraocular lens 12 to the inserter 14.

Referring again to FIG. 1, the inserter 14 preferably comprises a pushrod 50 with a tip 52 that is preferably attached at the proximal end 24 of the handpiece 20. With the inserter 14 in the second position 42, the tip 52 of the pushrod 50 traverses substantially along the longitudinal axis CH and may be used to advance the intraocular lens 12 down the nosepiece 30 and into the eye. The handpiece 20 of the inserter 14 directs the tip 52 of the pushrod 50 along the longitudinal axis CH towards the distal end 28 and into the load chamber 34, where the tip 52 engages the intraocular lens 12 during delivery of the intraocular lens 12.

In certain embodiments, the pushrod 50 may be configured to traverse through the nosepiece 30 when the nosepiece 30 is in the first position. In such embodiments, for example, the tip 52 may be used to control one or more of the haptics of the intraocular lens 12 during transfer from the lens case 18. The pushrod 50 may also be used to help maintain the nosepiece 30 in the first position 41, as illustrated in FIG. 1.

The tip 52 of the pushrod 50 may engage the intraocular lens 12 using any of the devices or methods known in the art. For example, the tip 52 of the pushrod 50 may either push against an edge portion of the intraocular lens 12. Alternatively, the tip 52 of the pushrod 50 may engage an inner portion of the intraocular lens 50 in order to more evenly distribute the pushing force over a greater area of the lens surface. In other embodiments, the tip 52 of the pushrod 50 does not directly contact the intraocular lens 12, but instead engages an intermediate device or substance, such as a viscoelastic, that distributes pressure across the intraocular lens 12 that causes it to proceed through the nosepiece 30 and into the eye.

The inserter 14 is adapted to receive the intraocular lens 12 from the lens case 18 and to deliver the intraocular lens into the eye after the natural lens has been removed. The inserter 14 and its various components may be made of any of the materials common in the art such as plastic or metal. Plastic materials are preferable if the inserter 14 is made for one-time use or a limited number of uses before disposing of the inserter 14. Metal material are preferable if the inserter is constructed for reuse, where the inserter 14 is sterilized prior to each use using either heat and/or sterilizing agents such as alcohol.

The longitudinal axis CN of the nosepiece 30 is preferably substantially centered within the handpiece 20. The term "substantially centered," as used here, means that a small amount of translational or rotational offset may be present in certain embodiments when the nosepiece 30 is in at least one of the first and second positions 41, 42. For instance, a small amount of translational or rotational offset may be used to provide a predetermined amount of transverse force between the tip 52 of the pushrod 50 and at least some portion of the nosepiece 30, as describe in further detail below herein.

The nosepiece 30 may be coupled to the handpiece 20 using devices and means known to those of skill in the art. In certain embodiments, the nosepiece 30 is lockably coupled to the handpiece 20 when the nosepiece 30 is in at least one of the first position 41 and the second position 42. The means or devices used to lock the nosepiece 30 in the first and/or second positions 41, 42 preferably provide a locking force of sufficient magnitude to substantially prevent the nosepiece 30 from moving during loading of the intraocular lens 12 into the nosepiece 30 and/or delivery of the intraocular lens 12 into the eye. Preferably, the magnitude of the locking force is low enough to allow relatively easy manipulation of the nosepiece 30 between the first and second positions 41, 42. Alternatively, the nosepiece 30 may be locked in the first and/or second positions using a lock mechanism or device (e.g., a pin or spring latch) that may be released or disengaged when manipulating the nosepiece 30 between the first and second positions 41, 42. In one embodiment, the nosepiece 30 is locked in the first position 41 by either pressing the tip 52 of the pushrod 50 against the delivery port 44 of the nosepiece 30 or by at least partially traversing the pushrod 50 through the delivery channel 43 of the nosepiece 30.

In certain embodiments, the nosepiece 30 has a longitudinal axis CN that is preferably substantially coaxial with the longitudinal axis CH of the handpiece 20 when the nosepiece 30 is in either the first position 41 or the second position 42. The term "substantially coaxial" as used herein means that the axes CH and CN are coaxial or that there is an offset angle between the axes CH and CN when the nosepiece 30 is in at least one of the first position 41 and the second position 42. The offset angle between the axes CH and CN, as measured in either a clockwise or counter-clockwise direction, is preferably at least about 10 degrees, more preferably less than about 5 degrees, and even more preferably less than about 2 degree. In one embodiment, an offset angle exist between the axes CH and CN when the nosepiece 30 is in the second position 42 such that the pushrod 50 produces a transverse force on at least some portion of the nosepiece 30, such as the delivery channel 43, as the pushrod 50 advances along the longitudinal axis CH. This transverse force may be advantageously used to prevent the tip 52 of prevent the tip 52 of the pushrod from moving on top of a portion of the intraocular lens 12 during delivery into the eye.

The nosepiece 30 may further comprise an outer surface 57 that substantially surrounds the load chamber 34 and the delivery channel 43. Preferably, the outer surface 57 is generally smooth and tapers from one end of the nosepiece 30 (e.g., near the transfer interface 36) having a relatively large cross-section, to an opposite end (e.g., near the delivery port 44) having a relatively small cross-section. The relatively small cross-section allows, among other things, the nosepiece 30 to be inserted into a relatively small incision in the eye, while the relatively large cross-section allows the intraocular lens 12 to be loaded into the load chamber 34 of the nosepiece 30 in a substantially uncompressed state. The outer surface 57 of the nosepiece 30 may further comprise a top face 58 and a bottom face 60 containing one or more openings 62. The openings 62 may be in the form of an aperture, notch, or some other type of void for providing at least partial access to the load chamber 34 and/or the delivery channel 43. For example, referring to FIGS. 1 and 2, the bottom face 60 is disposed below the load chamber 34 and comprises an aperture 64 that is rectangular in shape. The aperture 64 may, of course, take other shapes such as circle or a slit. As illustrated in FIG. 2, the top face 58 is disposed above the load chamber 34 and comprises an elongated notch 66. In other embodiments, for example as illustrate in FIG. 6, the elongated notches 66 are disposed on both the top and bottom faces 58, 60. In still other embodiments, there is only one opening 62 on either the top face 58 or the bottom face 60. Alternatively, one or more openings may be disposed at locations other than or in addition to the top and bottom faces 58, 60, for instance, on the sides of the outer surface between the top and bottom faces 58, 60.

The openings 62 may be used to visually inspect the insides of load chamber 34 prior to, during, or after transfer of the intraocular lens 12 into the nosepiece 30. The opening 62 may also be used to introduce one or more substances, for example a viscoelastic, into the load chamber 34 or some other portion of the nosepiece 30. Such substances may be introduced into the load chamber 34 from the transfer interface 36 of the load chamber 34 and visually inspected via the opening 62. The opening 62 may also be used as an overflow port through which excess amounts of injected substances exit the load chamber 34. Other uses of the opening 62 are consistent with embodiments of the inserter 14 or the insertion system 10. For instance one or more openings 62 may be configured to receive inspection instruments or tools for manipulating or otherwise preparing the intraocular lens 12 for delivery through the delivery channel 43 and into the eye. The opening 62 may also be used to aid in alignment of inserter 14 components when the nosepiece 30 is in either the first or second positions 41, 42.

Figure 7:
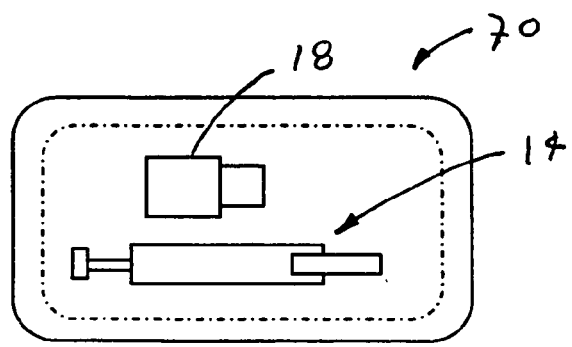
FIG. 7 is a top view of a container according to an embodiment of the invention for holding an inserter and a lens case.

Referring to FIG. 7, in certain embodiments, the insertion system 10 further comprises a container 70 for holding the inserter 14 and the lens case 18. For example, the container 70 may be in the form of a shrink-wrap package 70 illustrated in FIG. 7 and comprising top and bottom sheets of material that envelop the inserter 14 and the lens case 18. The inserter 14 and the lens case 18 are preferably placed inside the container 70 in a sterile environment and sealed in a manner that maintains the sterility of the inserter 14 and the lens case 18 until they are ready for use. Alternatively, the inserter 14 and the lens case 18 may be sterilized after being enclosed inside the container 70.

The container 70 may be made of plastic, metal, or any other suitable material suitable for sealing the inserter 14 and the lens case 18 and providing a sterile environment during storage. Combinations of such material are also possible. For example, the bottom sheet of the shrink-wrap package 70 may be made of a metal foil, while the top sheet is made of a transparent plastic material that is bondable to the metal foil, thus allowing visible inspection of the inserter 14 and the lens case 18 while inside the container 70. The container 70 may take other configurations, besides that illustrated in FIG. 7, for example a cardboard box.

Figure 8:
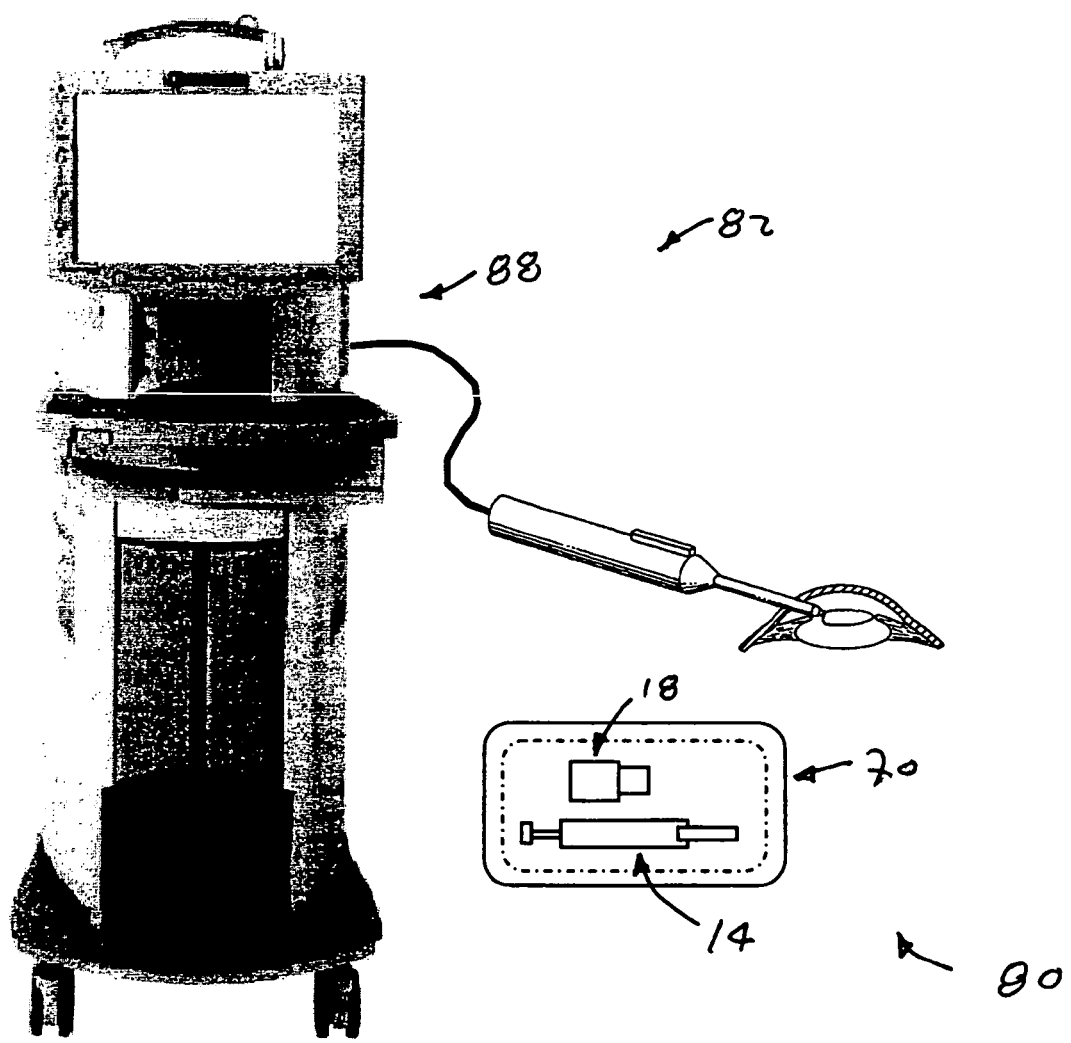
FIG. 8 illustrates a system according to the present invention for performing an ocular surgery.

Referring to FIG. 8, in certain embodiments, a system 80 for performing an ocular surgery comprises a phacoemulsification system 82 having a handpiece 84 for removing the natural lens of an eye and an electronic controller 88 for controlling the fluidics of handpiece 84 and/or the phacoemulsification power into the handpiece 84. The system 80 further comprises at least one inserter, such as the inserter 14, and at least one lens case, such as the lens case 18, wherein the lens case 18 preferably has an intraocular lens enclosed therein. The system 80 may include a plurality of lens cases, such as the lens case 18, and/or inserters, such as the inserter 14. Alternatively, the system 80 may include a plurality of containers 70, each containing at least one inserter 14 and at least one lens case 18, preferably containing an intraocular lens therein. Such configurations allow a practitioner to perform multiple surgeries. In certain embodiments, the controller 88 controls the delivery of electrical power into a transducer, such as a piezo-electric driver, that is part of the handpiece 84. In such embodiments, the piezo-electric driver changes size in accordance with changes in the electrical voltage and/or current provided by the controller 88. The controller 88 may also be used to control and/or monitor the irrigation fluid entering the eye and/or the aspiration used to remove fluid from the eye.

Figure 9:
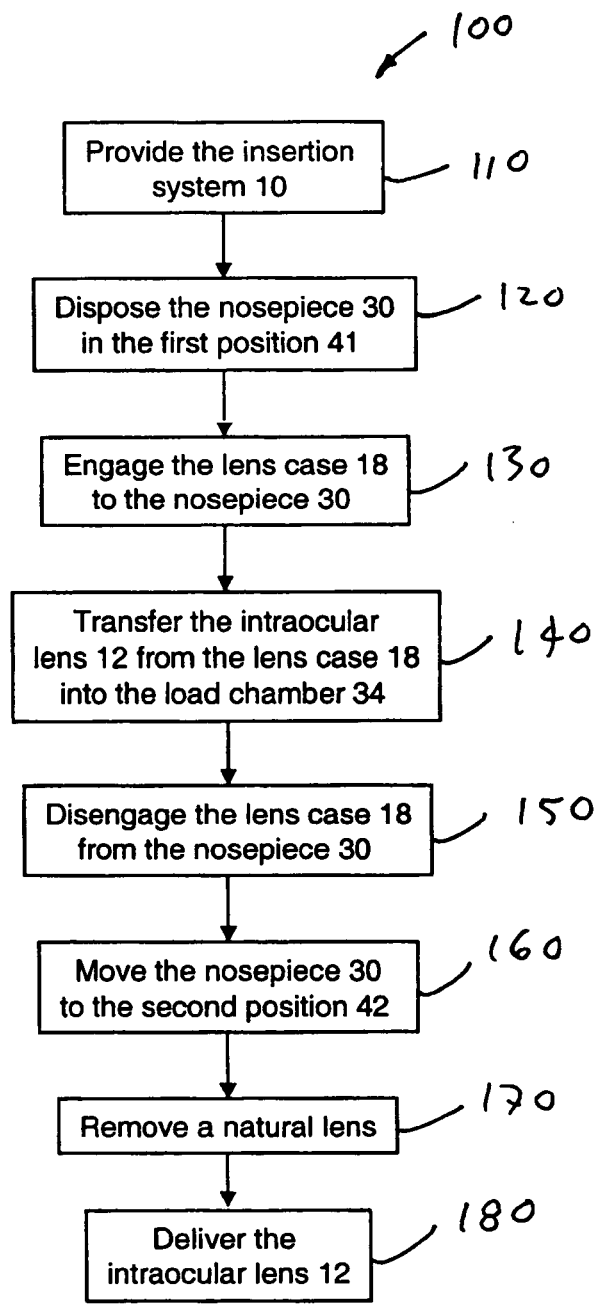
FIG. 9 is a block diagram illustrating a method according to an embodiment of the present invention for delivering an intraocular lens into eye of a subject.

Referring to FIG. 9, in certain embodiments, a method 100 for delivering the intraocular lens 12 into the eye of a subject comprises an operational block 110, which comprises providing the insertion system 10, including the inserter 14 and the lens case 18. The method 100 further comprises an operational block 120, which comprises disposing the nosepiece 30 in the first position 41, with the delivery channel 43 being disposed along the longitudinal axis CH. The method 100 also comprises an operational block 130, which comprises engaging the lens case 18 to the nosepiece 30 such that the transfer port 40 of the lens case 18 operably connected to the transfer interface 36 of the load chamber 34. The method 100 further comprises an operational block 140, which comprises transferring the intraocular lens 12 from the lens case 18 into the load chamber 34. The method 100 additionally comprises an operational block 150, which comprises disengaging the lens case 18 from the nosepiece 30. The method 100 also comprises an operational block 160, which comprises moving the nosepiece 30 to the second position 42, which is suitable for delivering the intraocular lens 12 into the eye of a subject.

In certain embodiments, the method 100 may additionally comprise an operational block 170, which comprises removing a natural lens from the eye of a subject. In other embodiments, the method 100 may additionally comprise an operational block 180, which comprises delivering the intraocular lens 12 into the eye of a subject.

In operational block 110, the insertion system 10 may be packaged in a container such as the container 70 illustrated in FIG. 7. Preferably, the intraocular lens 12 is preloaded in the lens case 18 by the manufacturer such that the intraocular lens 12 is in a sterile, unstressed environment.

In operational block 120, the nosepiece 30 is oriented in the first position 41, as illustrated in FIG. 1. By disposing the nosepiece 30 in this position, the load chamber 34 and the transfer interface 36 are distally located from the remaining portions of the inserter 14 and are thus readily accessible for transfer of the intraocular lens 12 from the lens case 18.

Figure 10:
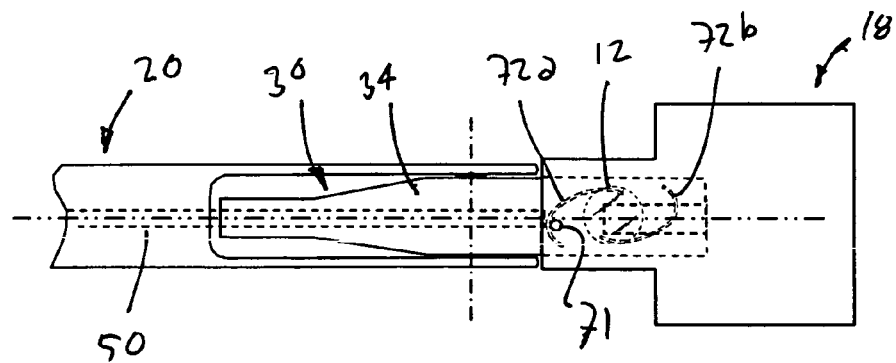
FIG. 10 is a top, magnified view of the insertion system shown in FIG. 1 illustrating engagement of the lens case with the nosepiece.

Referring to FIG. 10, in operational block 130, lens case 18 is engaged with the nosepiece 30. During engagement, the lens case 18 may at least partially surround the load chamber 34 of the nosepiece 30 such that the transfer interface 36 of the load chamber 34 is aligned and/or coupled to the transfer port 40 of the lens case 18. The engagement may be secured by means for at least partially locking the lens case 18 and the nosepiece 30 together, for example through the use of detents or spring loading. In certain embodiments, the load chamber 34 at least partially engages the nosepiece 30 prior to use by a practitioner and/or before shipment by the manufacturer or distributor. In such embodiments, the lens case 18 may be more fully engaged with the nosepiece 30 at operational block 130 of the method 100 or, alternatively, the operational block 130 becomes unnecessary altogether.

In operational block 140, the intraocular lens 12 is transferred from the lens case 18 and into the load chamber 34 of the nosepiece 30 in preparation for delivery of the intraocular lens 12 into the eye of a subject. This operation may be totally distinct from the engagement of the lens case 18 with the nosepiece 30 (operational block 130) or may occur simultaneously with the lens case 18 is engaged with the nosepiece 30. In certain embodiments, the tip 52 of the pushrod 50 may be used to manipulate one or more haptics 72a, 72b of the intraocular lens 12 either during transfer of the intraocular lens 12 from the lens case 18 to the load chamber 34 and/or subsequent to the delivery of the intraocular lens 12 into the load chamber 34.

Figure 11:
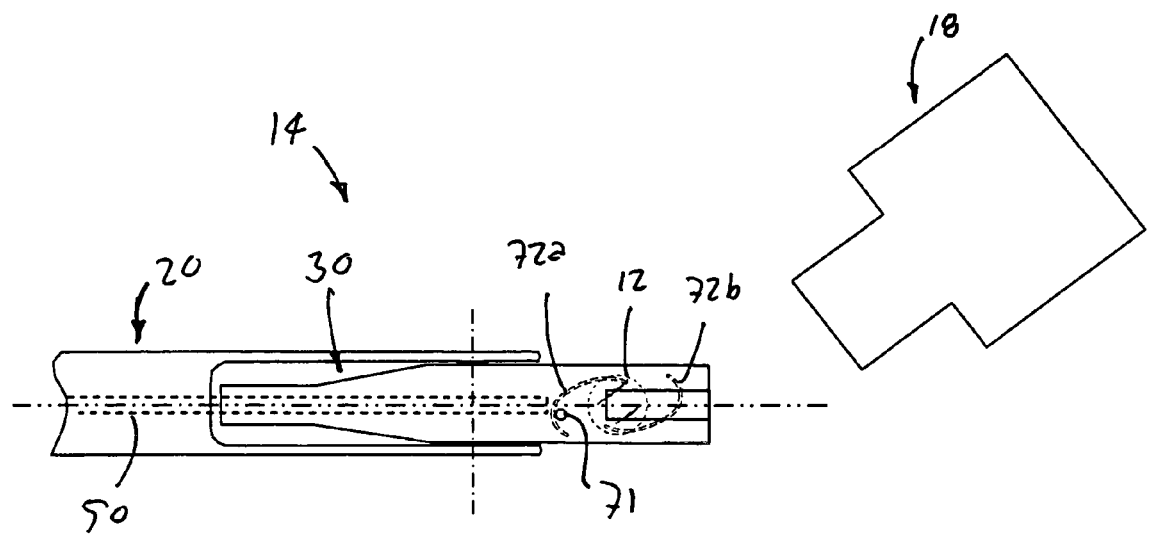
FIG. 11 is a top, magnified view of the insertion system shown in FIG. 1 illustrating disengagement of the lens case from the nosepiece.

Referring to FIG. 11, in operational block 150, the lens case 18 is disengaged or separated from the nosepiece 30. After disengagement, the lens case 18 may be disposed of or prepared for receiving a new lens in the same or a subsequent surgery. Structure and/or means may be provided for maintaining the intraocular lens 12 within the load chamber 34 of the nosepiece 30 upon disengagement of the load chamber 34 from the nosepiece 30. For instance, the load chamber 34 may contain one or more catches, hooks, or similar structures for engaging one or more haptics 72a, 72b of the intraocular lens 12 as it moves into the load chamber 34. For example, FIGS. 10 and 11 illustrate a catch 71 that engages the haptic 72a of the intraocular lens 12. During the loading of the intraocular lens 12 into the load chamber 34, the leading edge of the haptic 72a advances past the catch 71 in a way that prevents or impedes the intraocular lens 12 from sliding back towards the aperture 48 of the load chamber 34. In certain embodiments, the catch 71 may be part of the distal tip 52 of the pushrod 50.

Referring again to FIGS. 4 and 5, in operational block 160, the nosepiece 30 moved to the second position so that the intraocular lens may be delivered into the eye of a subject. As illustrated in FIG. 4, moving the nosepiece 30 to the second position 42 preferably comprises rotating the nosepiece 30 about the rotational axis CR to the second position 42, as illustrated in FIG. 5. As seen in FIG. 4, the nosepiece 30 is preferably rotated in a direction such that load chamber 34 and the intraocular lens 12 are disposed above the longitudinal axis CH of the handpiece 20 during rotation from the first position 41 to the second position 42. Alternatively, rotation in the opposite direction may also be used to rotate the nosepiece 30 from the first position 41 to the second position 42. In certain embodiments, the nosepiece 30 rotates between the first position 41 and the second position 42 about the rotational axis CR by approximately 180 degrees. In other embodiments, the nosepiece 30 rotates greater or less than 180 degrees, preferably in the range of about 170 degrees or less to about 190 degrees or more, more preferably about 175 degrees to about 185 degrees, and even more preferably between about 178 degrees and about 182 degrees.

In certain embodiments, the nosepiece 30 moves or rotates between the first position 41 and the second position 42 in an automated or semi-automated fashion. For example, the handpiece 20 may be configured such that nosepiece 30 rotates from the first position 41 to the second position 42 as the pushrod 50 traverses the longitudinal axis CH of the handpiece 20. This may be accomplished, for instance, by using a spring, cam, and/or linkage mechanism that is engaged by the pushrod 50 as is nears the nosepiece 30.

Referring again to FIG. 5, in certain embodiments, moving or rotating the nosepiece 30 from the first position 41 to the second position 42 transversely displaces at least a portion of the haptic 72b from the pushrod 50. For instance, by rotating the nosepiece 30 in the direction indicated in FIG. 4, the haptic 72b may be disposed above the pushrod 50 as the nosepiece 30 arrives at the second position 42 and is pushed in an upward direction by the pushrod 50. By disposing the haptic 72b above the pushrod 50, the intraocular lens 12 is advantageously positioned so that the haptic 72b is not deformed or damaged by the pushrod 50 when the pushrod 50 advances the intraocular lens 12 down the delivery channel 43 for delivery into the eye. This geometry between the pushrod 50 and the haptic 72b is accomplished simply by moving the nosepiece 30 from the first position 41 to the second position 42, with little or no additional manipulation of the haptic 72b by a practitioner, such as a surgeon or assisting nurse. Alternatively, the tip 52 of the pushrod 50 may be moved proximally along the longitudinal axis CH or otherwise adjusted to obtain a predetermined geometric relationship between the intraocular lens 12 and the tip 52 of the pushrod 50. For example, the tip 52 of the pushrod 50 may initially be disposed along a portion of the optic body of the intraocular lens 12 when the nosepiece 30 is rotated from the first position 41 to the second position 42. Subsequently, the tip 52 of the pushrod 50 may then be retracted slightly such that the tip 52 engages or is disposed along the edge of the optic body of the intraocular lens 12.

In certain embodiments, the nosepiece 30 may be configured to be movable between the first position 41 and the second position 42 in a manner that combines both rotation and translation of the nosepiece 30. For example, the nosepiece 30 may be rotated from the first position 41 by approximately 180 degrees and then pushed back distally along the longitudinal axis CH of the handpiece 20. The translation motion may be used, for instance, to secure the nosepiece 30 against the body of the handpiece 20 in preparation for delivery of the intraocular lens 12. Other combinations of rotation and/or translation may be use for moving the nosepiece 30 between the first position 41 and the second position 42.

In operational block 170, the natural lens may be removed, for instance by providing the phacoemulsification system 82. In such instances, the handpiece 84 is used to remove the natural lens of the eye and is under the control of the electronic controller 88, which may be used to control the fluidics of the handpiece 84 and/or the power into the handpiece 84. In certain embodiments, the controller 88 is used to adjust the fluidics of the handpiece 84 and/or power into the handpiece 84 in accordance to system conditions. The amount of power into the handpiece 84 and/or the fluidics of the handpiece 84 may be changed due to the presence of an occlusion in an aspiration line, for example, as disclosed in U.S. Pat. No. 5,700,240, herein incorporated by reference. The removal of the natural lens may be performed before, during, or after the other operational blocks of the method 100. For instance, a nurse or assistant may perform operational blocks 110 through 160 while a surgeon is performing operational block 170. In certain embodiments, the natural lens is not removed or has been removed during a previous surgery and the method 100 would not include the operational block 170. For instance, the intraocular lens 12 may be phakic intraocular lens (e.g., an intraocular lens that is delivered into an eye still containing the natural lens) or a lens that is used to supplement another intraocular lens placed into the eye during a previous surgery.

In operational block 180, the intraocular lens 12 is delivered into the eye by advancing the lens down the delivery channel 43 using the pushrod 50 until the lens passes through the delivery port 44 and into the eye. The tip 52 of the pushrod 50 may have any of the various configurations used in the art or incorporate an innovative configuration designed to provide a predetermined advantage. In certain embodiments, the tip 52 of the pushrod 50 may be made of a relatively soft material and/or be disposed to engage a portion of the intraocular lens 12, for example a fold in the body of the intraocular lens. In other embodiments, the tip 52 of the pushrod 50 may be made of a relatively hard material and/or be disposed to engage an edge or peripheral portion of the intraocular lens 12. The specific characteristics of the pushrod 50 and the tip 52 may be selected depending on the type of intraocular lens being delivered, for example, depending or whether the intraocular lens 12 is made of silicone based material or a relatively stiffer material such as an acrylic based material. Other parameters of the intraocular lens 12 may also be used in determining the specific characteristics of the pushrod 50 and the tip 52.

During delivery of the intraocular lens 12 into the eye, the pushrod 50 is preferably substantially disposed along the longitudinal axis CH. In certain embodiments, the tip 52 and/or the pushrod 50 may be configured to provide a biasing force against at least a portion of the delivery channel 43 during delivery of the intraocular lens 12. Such a biasing force may be used to prevent the tip 52 of the pushrod 50 from moving onto the intraocular lens 12, for example, when the intraocular lens 12 is made of an acrylic material and/or the tip 52 is made of a relatively hard material. In certain embodiments, at least a portion of the pushrod 50, for example the tip 52 of the pushrod 50, may be offset asymmetrically from the longitudinal axis CH. In other embodiments, at least a portion of the pushrod 50 may have an offset angle relative to the longitudinal axis CH. In yet other embodiments, a portion of the inserter 14, for example the delivery channel 43, may have an offset angle relatively to at least one of the longitudinal axis CH and a longitudinal axis along which the tip 52 of the pushrod 50 travels.

The method 100 may additionally comprise introducing one or more substances, for example a viscoelastic, into at least a portion of the nosepiece 30 and/or the lens case 18. The substance may be introduced at any time or at various times during the method 100, for example through one or more of the openings 62 or through the transfer interface 36 of the load chamber 34.

Figure 12:
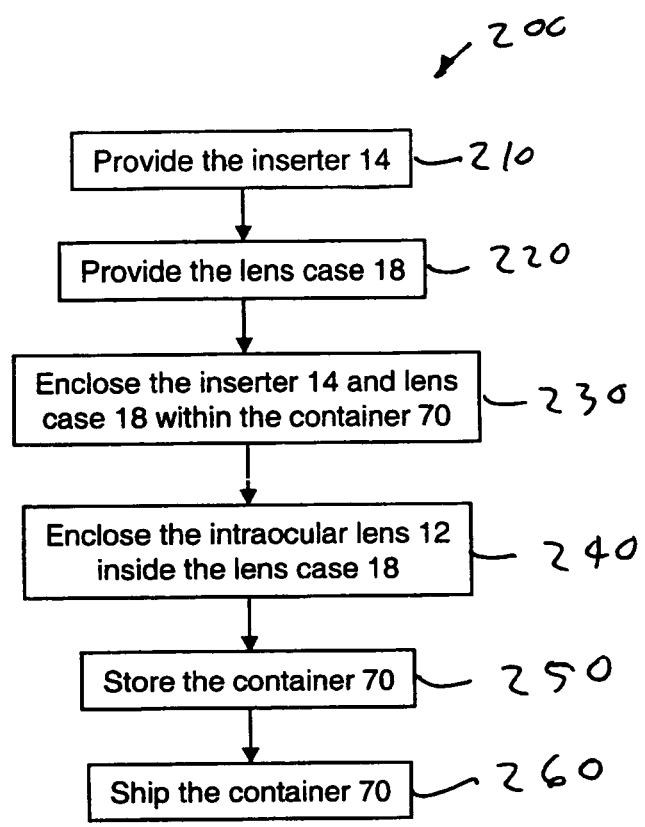
FIG. 12 is a block diagram illustrating a method according to an embodiment of the present invention for packaging an insertion system for delivery of an intraocular lens into the eye of a patient.

Referring to FIG. 12, in certain embodiments, a method 200 for packaging the insertion system 10 comprises an operational block 210, which comprises providing the inserter 14. The method 200 further comprises an operational block 220, which comprises providing the lens case 18. The method 200 also comprises an operational block 230, which comprises enclosing the inserter 14 and lens case 18 within the container 70.

In certain embodiments, the method 200 additionally comprises an operational block 240, which comprises enclosing the intraocular lens 12 inside the lens case 18. The method 200 may also comprise an operational block 250, which comprises storing the container 70, and/or an operational block 260, which comprises shipping the container 70.

In operational block 230, the inserter 14 and the lens case 18 are enclosed in the container 70, as illustrated in FIG. 7 and described in greater detail above herein. The inserter 14 and the lens case 18 are preferably packaged such that they are separate from one another; however, other configurations are possible. For example, the inserter 14 and the lens case 18 may be placed adjacent to one another and sealed so as to provide a container 70 that is relatively small. Also, the lens case 18 and the nosepiece 30 may be coupled together prior to shipment to a practitioner and placed and/or sealed inside the container 70.

In operational block 240, the lens case 18 preferably contains a lens, for example the intraocular lens 12, prior to packaging inside the container 70. Preferably, the intraocular lens 12 is disposed inside the lens case 18 prior to shipment by the manufacturer or distributor, so as to advantageously maintain the intraocular lens 12 in a sterile environment until ready for use by a practitioner or their assistant. The intraocular lens 12 may be maintained in a low stress or essentially stress free state inside the lens case 18, allowing the intraocular lens 12 to be stored over long periods of time without unwanted permanent deformation that could reduce visual acuity or perception inside the eye.

In operational block 250, the container 70 is stored till ready for shipment, distribution, or use. In operational block 260, the container 70 is shipped by the manufacturer or distributor either individually, as a part of a set of containers 70, or as part of the phacoemulsification system 80. In certain embodiments, several lens cases 18, each containing a different intraocular lens 12, may be packaged, stored, and/or shipped together to a customer or storage location. Each container 70 may contain an intraocular lens 18 having the same optical power as other containers 70. Alternatively, each container 70 may have a predetermined optical power that is different from other containers 70.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that described above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. An inserter for delivering an intraocular lens into the eye of a subject, comprising:
   a handpiece having a longitudinal axis, a proximal end, and a distal end;
   a nosepiece having a proximal end, and a distal end, wherein the nosepiece is disposed at the distal end of the handpiece and having a rotational axis substantially perpendicular to the longitudinal axis and a load chamber with a transfer interface for receiving an intraocular lens comprised of one or more haptics, wherein the load chamber is comprised of one or more catches for engaging the one or more haptics of the intraocular lens, wherein the one or more catches are configured such that a leading edge of the one or more haptics advance past the one or more catches in a way that impedes the intraocular lens from sliding back; and
   wherein the nosepiece is adapted to rotate approximately 180 degrees about the rotational axis between a first position for loading the intraocular lens and a second position for delivering the intraocular lens into the eye of a subject.

2. The inserter of claim 1, wherein the nosepiece further comprises a delivery channel for delivering the intraocular lens into the eye, the delivery channel having a delivery port with a cross-sectional area that is less than a cross-sectional area of the load chamber.

3. The inserter of claim 2, wherein the delivery channel comprises a smoothly tapered portion extending from the load chamber.

4. The inserter of claim 2, wherein the delivery channel is substantially disposed along the longitudinal axis when the nosepiece is disposed in the first position and when the nosepiece is disposed in the second position.

5. The inserter of claim 2, wherein the transfer interface comprises an aperture that is substantially center along the longitudinal axis and distally located relative to the delivery channel when the nosepiece is in the first position.

6. The inserter of claim 1, wherein the longitudinal axis and the rotational axis substantially intersect.

7. The inserter of claim 1, wherein the nosepiece is lockably coupled to the handpiece when the nosepiece is in at least one of the first position and the second position.

8. The inserter of claim 1, further comprising a pushrod for moving the intraocular lens through the load chamber.

9. The inserter of claim 8, wherein the inserter is adapted such that at least a portion of the one or more haptics of the intraocular lens is transversely displaced from the pushrod when the nosepiece is in the second position.

10. The inserter of claim 8, wherein the pushrod is disposed to traverse the load chamber when the nosepiece is in the first position.

11. The inserter of claim 1, wherein the longitudinal axis is substantially centered within the handpiece.

12. The inserter of claim 1, wherein the nosepiece further comprises a top face and a bottom face.

13. The inserter of claim 12, further comprising an opening disposed on at least one of the top face and the bottom face.

14. An insertion system for delivering an intraocular lens into the eye of a subject, comprising:
an inserter for delivering an intraocular lens comprised of one or more haptics into an eye, having:
a handpiece having a longitudinal axis, a proximal end, and a distal end;
a nosepiece having a proximal end, and a distal end, wherein the nosepiece is disposed at the distal end of the handpiece and having a rotational axis substantially perpendicular to the longitudinal axis and a load chamber with a transfer interface for receiving the intraocular lens; wherein the load chamber is comprised of one or more catches for engaging the one or more haptics of the intraocular lens, wherein the one or more catches are configured such that a leading edge of the one or more haptics advance past the one or more catches in a way that impedes the intraocular lens from sliding back;
wherein the nosepiece is adapted to rotate approximately 180 degrees about the rotational axis between a first position for loading the intraocular lens and a second position for delivering the intraocular lens into the eye of a subject; and
a lens case for holding the intraocular lens, the lens case having a transfer port for transferring the intraocular lens from the lens case into the load chamber.

15. The insertion system of claim 14, further comprising an intraocular lens disposed inside the lens case.

16. The insertion system of claim 15, wherein the lens case is adapted to engage the nosepiece at the transfer interface when the nosepiece is in the first position.

17. The insertion system of claim 16, wherein the lens case is adapted to disengage the nosepiece for transfer of the intraocular lens into the delivery chamber.

18. The insertion system of claim 15, wherein the lens case is adapted to transfer the intraocular lens into the load chamber when the nosepiece is in the first position.

19. The insertion system of claim 14, further comprising a cover disposed over the transfer port.

20. The insertion system of claim 14, further comprising a container for holding the inserter and the lens case.

21. The insertion system of claim 14, wherein the lens case and the nosepiece are at least partially engaged prior to shipment to a practitioner.

22. An inserter for delivering an intraocular lens into an eye, comprising:
a handpiece having a longitudinal axis substantially centered within the handpiece, a proximal end, and a distal end;
a nosepiece disposed at the distal end of the handpiece and the nosepiece having a longitudinal axis and a load chamber with a transfer interface for receiving an intraocular lens comprised of one or more haptics, wherein the load chamber is comprised of one or more catches for engaging the one or more haptics of the intraocular lens, wherein the one or more catches are configured such that a leading edge of the one or more haptics advance past the one or more catches in a way that impedes the intraocular lens from sliding back;
wherein the nosepiece is movable between a first position for loading the intraocular lens and a second position for delivering the intraocular lens into the eye of a subject; and
the longitudinal axis of the handpiece and the longitudinal axis of the nosepiece being substantially coaxial when the nosepiece is in the first position and the second position.

23. The inserter of claim 22, further comprising an offset angle between the longitudinal axis of the handpiece and the longitudinal axis of the nosepiece when the nosepiece is in at least one of the first position and the second position.

24. The inserter of claim 23, wherein the offset angle is less than at least about 10 degrees.

25. The inserter of claim 23, wherein the offset angle is less than about 1 degree.

26. An inserter for delivering an intraocular lens into an eye, comprising:
a handpiece having a longitudinal axis substantially centered within the handpiece, a proximal end, and a distal end;
a nosepiece having a proximal end, and a distal end, wherein the nosepiece is disposed at the distal end of the handpiece and having a rotational axis substantially perpendicular to the longitudinal axis and a load chamber with a transfer interface for receiving an intraocular lens comprised of one or more haptics, the rotational axis substantially intersecting the longitudinal axis, wherein the load chamber is comprised of one or more catches for engaging the one or more haptics of the intraocular lens, wherein the one or more catches are configured such that a leading edge of the one or more haptics advance past the one or more catches in a way that impedes the intraocular lens from sliding back; and
wherein the nosepiece is adapted to rotate about the rotational axis between a first position for loading the intraocular lens and a second position for delivering the intraocular lens into the eye of a subject.

* * * * *